(12) United States Patent
Barrett et al.

(10) Patent No.: US 8,130,369 B2
(45) Date of Patent: Mar. 6, 2012

(54) MEASURING HEMATOCRIT AND ESTIMATING HEMOGLOBIN VALUES WITH A NON-INVASIVE, OPTICAL BLOOD MONITORING SYSTEM

(75) Inventors: Louis LeeGrande Barrett, West Point, UT (US); David Wayne Peterson, Clinton, UT (US); Kristian Allen Sammann, Murray, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 470 days.

(21) Appl. No.: 12/265,392

(22) Filed: Nov. 5, 2008

(65) Prior Publication Data

US 2010/0110416 A1    May 6, 2010

(51) Int. Cl.
*G01N 33/48* (2006.01)
(52) U.S. Cl. .............................. 356/39; 436/70
(58) Field of Classification Search .............. 356/39–42; 436/70
See application file for complete search history.

(56) References Cited

U.S. PATENT DOCUMENTS

| | | | | |
|---|---|---|---|---|
| 5,171,456 A | * | 12/1992 | Hwang et al. | 210/782 |
| 5,351,686 A | * | 10/1994 | Steuer et al. | 600/310 |
| 5,372,136 A | | 12/1994 | Steuer et al. | |
| 5,476,764 A | * | 12/1995 | Bitensky | 435/2 |
| 5,676,644 A | * | 10/1997 | Toavs et al. | 604/6.11 |
| 5,729,333 A | | 3/1998 | Osten et al. | |

FOREIGN PATENT DOCUMENTS

| | | |
|---|---|---|
| WO | 9427495 | 12/1994 |
| WO | 0187151 | 11/2001 |

OTHER PUBLICATIONS

Dirren H. Logman MHGM, et al. "Altitude Correction for Hemoglobin", European Journal of Clinical Nutrition, 1994; 48_625-632. (Believed to no longer be in publication.).
Peer Review "Effects of CPD and K3EDTA Preservatives on Blood Sample Hematocrit", Asaio Abstract Submission Information, 45th Annual Conference, San Diego, Jun. 3-5, 1999.
S. Zhang, Ph.D. et al. Hematocrit Measurement Error Due to Time Dependence of Hematocrit for EDTA-Preserved Blood Samples, ANS 36 Annual Meeting & Scientific Exposition, http://www.call4abstracts.com/ans/main/finalpreview, site visited Jun. 25, 2003.
Crit-Line Hematrocrt Accuracy, Hema Metrics, vol. 1, Tech Note No. 11 (Rev. D), pp. 1-4, Feb. 24, 2003.

* cited by examiner

*Primary Examiner* — Tarifur Chowdhury
*Assistant Examiner* — Michael P Lapage
(74) *Attorney, Agent, or Firm* — Leydig, Voit & Mayer, Ltd.

(57) ABSTRACT

An optical blood monitoring system with a ratiometric model determines hematocrit values for a hemodialysis patient, from which hemoglobin values for the patient are estimated. The ratiometric model is calibrated, normally against a cell counter, using blood from a blood bank. The blood from a blood bank is preserved in a long term preservative which is typically different than that found in clinical settings. The hematocrit value determined by the ratiometric model is scaled by scaling factor so that the estimated hemoglobin level output from the monitor consistently matches that measured in a clinical setting. The hematocrit scaling factor is substantially about 1.033 when the patient's blood sample is stored in a short term preservative ethylene diamine tetra acetic, and is substantially about 1.06 when the hematocrit is measured in the blood sample without preservative being added to the blood sample. The hemoglobin value can also be adjusted for altitude.

20 Claims, 6 Drawing Sheets

MEASURING HEMATOCRIT AND ESTIMATING HEMOGLOBIN VALUES WITH A NON-INVASIVE, OPTICAL BLOOD MONITORING SYSTEM

FIELD OF THE INVENTION

The invention relates to optical blood monitoring systems for hemodialysis patients, and in particular, to methods of measuring hematocrit and for estimating hemoglobin levels in real-time from the measured hematocrit value.

BACKGROUND OF THE INVENTION

Patients with kidney failure or partial kidney failure typically undergo hemodialysis treatment in order to remove toxins and excess fluids from their blood. To do this, blood is taken from a patient through an intake needle (or catheter) which draws blood from an artery located in a specifically accepted access location (for example, an arm, thigh, subclavian, etc.). The needle (or catheter) is connected to extracorporeal tubing that is fed to a peristaltic pump and then to a dialyzer which cleans the blood and removes excess water. The cleaned blood is then returned to the patient through additional extracorporeal tubing and another needle (or catheter). Sometimes, a heparin drip is located in the hemodialysis loop to prevent the blood from coagulating. By way of background, as the drawn blood passes through the dialyzer, it travels in straw-like tubes within the dialyzer which serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration.

It is known in the art to use an optical blood monitoring system during hemodialysis, such as the CRIT-LINE® monitoring system which is sold by the assignee of this application. The CRIT-LINE® blood monitoring system uses optical techniques to non-invasively measure in real-time the hematocrit level of blood flowing through a hemodialysis system. In the CRIT-LINE® system, a sterile, single-use blood chamber is attached in-line to the extracorporeal tubing on the arterial side of the dialyzer. The blood chamber provides a viewing point for optical sensors during the hemodialysis procedure. Multiple wavelengths of light are directed through the blood chamber and the patient's blood flowing therethrough, and a photo detector (or array of photo detectors) detects the resulting intensity of each wavelength. The preferred wavelengths are about 810 nm, which is substantially isobestic for red blood cells, and about 1300 nm, which is substantially isobestic for water. A ratiometric technique implemented in the CRIT-LINE® controller, substantially as disclosed in U.S. Pat. No. 5,372,136 entitled "System And Method For Non-Invasive Hematocrit Monitoring", which issued on Dec. 13, 1999 and is also assigned to the assignee of the present application, uses this information to calculate the patient's hematocrit value in real-time. The hematocrit value, as is widely used in the art, is the percentage determined by dividing the volume of the red blood cells in a given whole blood sample by the overall volume of the blood sample. The CRIT-LINE® system can also measure, optically, the oxygen saturation level in the blood flowing into the dialyzer.

In a clinical setting, the actual change in blood volume occurring during hemodialysis can be determined, in real-time, from the change in the measured hematocrit. Thus, a hemodialysis blood monitoring system which uses optical techniques, such as the CRIT-LINE® monitor, is able to monitor non-invasively, and in real-time, the patient's hematocrit level and in turn the accurate percentage change in blood volume during a hemodialysis treatment session. The ability to monitor change in blood volume facilitates safe, effective hemodialysis.

Hemoglobin is the iron containing oxygen transport contained in red blood cells, but constitutes less than 50% of the total content of the typical red blood cell. A decrease in hemoglobin, with or without an absolute decrease of red blood cells, can lead to anemia. The measured hematocrit (HCT), i.e. the portion of blood volume occupied by red blood cells, is typically about three times the hemoglobin (Hgb) level. It is widely assumed that HCT=2.941×Hgb at sea level. For example, when common blood tests are performed, a hemoglobin level measured at 17 grams per deciliter would normally correspond to a hematocrit (ratio of red cell volume to total blood volume) slightly less than 51 percent.

Hemoglobin levels can be measured in vitro directly from a patient's blood sample. When a blood sample is taken to a laboratory for lab work, direct hemoglobin measurements commonly require the lysing of red blood cells to free the hemoglobin into solution. The concentration of the hemoglobin in solution is then measured using assay techniques. Physicians typically monitor the Hgb level of anemic patients, and prescribe medication or other therapeutic care based at least in part on the patient's Hgb level.

Since optical hemodialysis blood monitoring is an in vivo process, it is important to maintain the integrity of the red blood cells flowing through the hemodialysis circuit during the monitoring process. Therefore, optical hemodialysis blood monitoring systems estimate hemoglobin levels based on the optically measured hematocrit (i.e., HCT=2.941*Hgb). The accuracy of the estimated hemoglobin levels is thus dependent upon the accuracy of the optically measured hematocrit.

Each optical blood monitoring system is calibrated for HCT by the manufacturer in-house before it is shipped. To calibrate, the manufacturer typical compares the system's output against in vitro lab work for the same blood sample. Typically, blood used for calibration is from a blood bank, and is preserved in a long-term preservative and anticoagulant, such as citrate phosphate dextrose (CPD) which includes nutrients to feed the blood. A cell counter, e.g. a Coulter counter, is normally used to determine the base line hematocrit values for calibrating purposes. The general formula for hematocrit is:

$$HCT = \frac{(RBC) \times (MCV)}{V} \quad \text{Eq. (1)}$$

where RBC is the red blood cell count in the blood sample, MCV is the mean cell volume of the measured red blood cells and V is the total volume of the sample. To measure hematocrit using a cell counter, a sample of blood is drawn from the patient into a test tube. The cell counter draws a metered volume (V) of the blood sample and red blood cells are literally counted as they drop through a small diameter pipette within the cell counter. This determines the red blood cell count (RBC) in the above Eq. (1). The average mean cell volume (MCV) is measured by running an electrical current through a designated area of the pipette. The size of the blood cell correlates to the amount of electrical current passed.

Through mathematical means within the cell counter, the measured RBC and MCV values are used to determine the hematocrit per the Eq. (1).

An optical blood monitoring system, such as the CRIT-LINE® monitoring system, is calibrated against the results of the cell counter (or other in vitro method) by adjusting a constant in a mathematical ratiometric model that runs on its controller. The mathematical ratiometric model for determining the hematocrit value can be represented by the following equation:

$$HCT = f\left[\frac{\ln\left(\frac{i_{800}}{I_{0800}}\right)}{\ln\left(\frac{i_{1300}}{I_{01300}}\right)}\right] \quad \text{Eq. (2)}$$

where $i_{800}$ is the light intensity of the photo receiver at 810 nm, $i_{1300}$ is the light intensity of the photo detector at 1300 nm and $I_{0800}$ and $I_{01300}$ are constants representing the light intensity incident on the blood accounting for losses through the blood chamber. The function f is a mathematical function which has been determined based on experimental data to yield the hematocrit value. In the above Eq. (2), the constants $I_{0800}$ and $I_{01300}$ are unknown values which can be adjusted for calibration. In addition to being used to measure hematocrit (HCT), the measured light intensity at the 810 nm wavelength is used in the CRIT-LINE® monitor to determine the oxygen saturation level. Therefore, for purposes of calibration, it is desirable to keep the constant $I_{0800}$ at a predetermined value. The constant $I_{0800}$ can be estimated by measuring $i_{800}$ through a blood chamber full of normal saline. Since no red cells are present, the measurement of $i_{800}$ is approximately equal to $I_{0800}$. The monitor is thus calibrated by adjusting the constant $I_{01300}$ in order that the hematocrit value (HCT) determined by Eq. (2) matches the hematocrit value HCT determined by the cell counter in Eq. (1). This method is quite accurate and repeatable for measured hematocrit calibration.

However, actual blood draws in a clinic are preserved in potassium ethylene diamine tetra acetic ($K_3$EDTA), which is a short-term preservative that does not change the morphology and optical characteristics of the red blood cells in the same manner as the long-term preservative CPD most often used to validate calibration by the manufacture. To account for this difference in preservatives, the prior art has often estimated the hemoglobin value from the measured hematocrit using a linear relationship (i.e. a slope of 3.000) with a positive offset correction of one hematocrit unit. For many applications to date, this estimation has been adequate.

A primary object of the invention is to better compensate, when measuring hematocrit values (HCT) and predicting hemoglobin values (Hgb) from the measured HCT, for differences between preservatives used during the calibration process and preservatives used in a clinical setting. Another object of the invention is to implement such improved compensation in an optical hemodialysis blood monitoring system, thereby providing more consistency between optically measured hematocrit and estimated hemoglobin values and those measured in vitro from a blood sample taken in a clinic.

SUMMARY OF THE INVENTION

The inventors have discovered that a linear slope adjustment, rather than an offset correction, is required to accurately account for differences in preservatives used when calibrating non-invasive, optical blood monitoring equipment and those typically used in a clinical setting when outputting a measured hematocrit value (HCT) from which a hemoglobin value (Hgb) is estimated. In order to compensate for differences in the anticoagulant used to preserve the blood used for calibration and the anticoagulant typically used in the clinical setting, the measured HCT is then multiplied by a scaling factor. In the preferred embodiment of the invention, the blood used for calibration is from a blood bank and it is preserved in the anticoagulant citrate phosphate dextrose (CPD) without additional preserving salts, and the scaling factor is set at 1.033 in order to correlate the HCT output on the display of the optical blood monitor with the expected measured hematocrit from a blood sample preserved in the anticoagulant potassium ethylene diamine tetra acetic ($K_3$EDTA) typically used with in vitro testing in the clinical setting.

The inventors have also discovered that a scaling factor of 1.06 is appropriate when comparing HCT measured on equipment calibrated with blood preserved in the aforementioned CPD formulation to HCT measured in whole blood without a preservative. It has also been found that the anticoagulant heparin has no effect, and requires no scaling to compensate for its use in estimating hemoglobin values from measured hematocrit values.

The use of a scaling factor, such as 1.033, to scale hematocrit values prior to estimating hemoglobin values from the measured hematocrit value is especially useful when using a non-invasive, optical blood monitoring system for monitoring a patient's blood during hemodialysis treatment. Hemodialysis patients are normally scheduled for treatment three times a week, either on a Monday-Wednesday-Friday schedule or a Tuesday-Thursday-Saturday schedule. The Hgb value output by the optical monitor is therefore available for the consideration of the attending physician at each treatment session without the need to draw a blood sample from the patient. As mentioned, the scaling factor removes statistical bias from the HCT and Hgb values output by the optical monitor, as compared to what the physician would expect from standard in vitro blood work.

As mentioned, such an optical system includes a blood chamber located inline with extracorporeal tubing through which a patient's blood flows during hemodialysis. An optical sensor assembly preferably monitors the blood flowing through the blood chamber. In the preferred embodiment, light is emitted at a first wavelength, substantially about 810 nm which is isobestic for red blood cells, and also at a second wavelength at substantially 1300 nm which is isobestic for water. The intensity of the light at these wavelengths is detected after it passes through the blood chamber and the blood flowing therethrough. The controller for the monitor includes a ratiometric model that determines a hematocrit value as a function of the detected light intensity at the first and second wavelengths as described above with respect to Eq. (2). As mentioned above, the ratiometric model is calibrated, preferably by adjusting the $I_{01300}$ value. During the calibration procedure, saline diluted samples of hemo-concentrated blood from a blood bank are used to baseline the calculated hematocrit value from the ratiometric model to the hematocrit value measured by an in vitro method (i.e., a cell counter). The blood from a blood bank is preserved in the anticoagulant CPD (without additional preserving salts). When using an optical blood monitor in the field, the ratiometric model is used to determine the hematocrit value based on the detective light intensity of the first and second wavelengths. Then, in accordance with the preferred embodiment of the invention, the hematocrit value (HCT) is scaled by a scaling factor of 1.033 in order to adjust the hematocrit reading (HCT) to correspond to a reading that would be expected from a sample of the patient's blood stored in a purple top test tube, i.e. one in which the blood taken from the patient is stored in $K_3$EDTA, as is typical in the clinical setting. The scaled hematocrit value ($HCT_s$) is then used to estimate hemoglobin, i.e. Hgb=$HCT_s$/2.941. In addition, if desired, the calculated hemoglobin value can also be corrected for altitude. This is preferably done using an altitude correction algorithm to determine a correction factor, which is added to the calculated hemoglobin value. At sea level, the correction factor is zero, however, at high altitudes, the effect is more substantial. If such an altitude algorithm is used, it is preferred that the user would enter the altitude at which the unit is operating at the time of installation.

As mentioned, it is also possible to scale the hematocrit level measured by the optical blood monitor by factor 1.06 in order to match a clinically determined hematocrit (HCT) for whole blood to which no preservative or anticoagulant has been added. While this may be desirable in some circumstances, most clinical data regarding hematocrit and hemoglobin is preserved in potassium ethylene diamine tetra acetic ($K_3$EDTA). Therefore, using a scaling factor of 1.033, it is particularly helpful to correlate and match optically determined hemoglobin levels (when the optical monitor is calibrated using blood from a blood bank preserved in CPD) with clinically determined hemoglobin levels (when the blood sample is preserved in $K_3$EDTA). In this case, as mentioned above, physicians may feel more comfortable relying on the immediate Hgb output displayed by the non-invasive, optical monitor, thereby obviating the physician's desire to draw a blood sample from the patient and order in vitro blood work.

Of course, the blood monitor preferably includes many other features known in the art. Other features and advantages of the invention may be apparent to those skilled in the art upon reviewing the following drawings and description thereof.

DETAILED DESCRIPTION OF THE DRAWINGS

Figure 1:
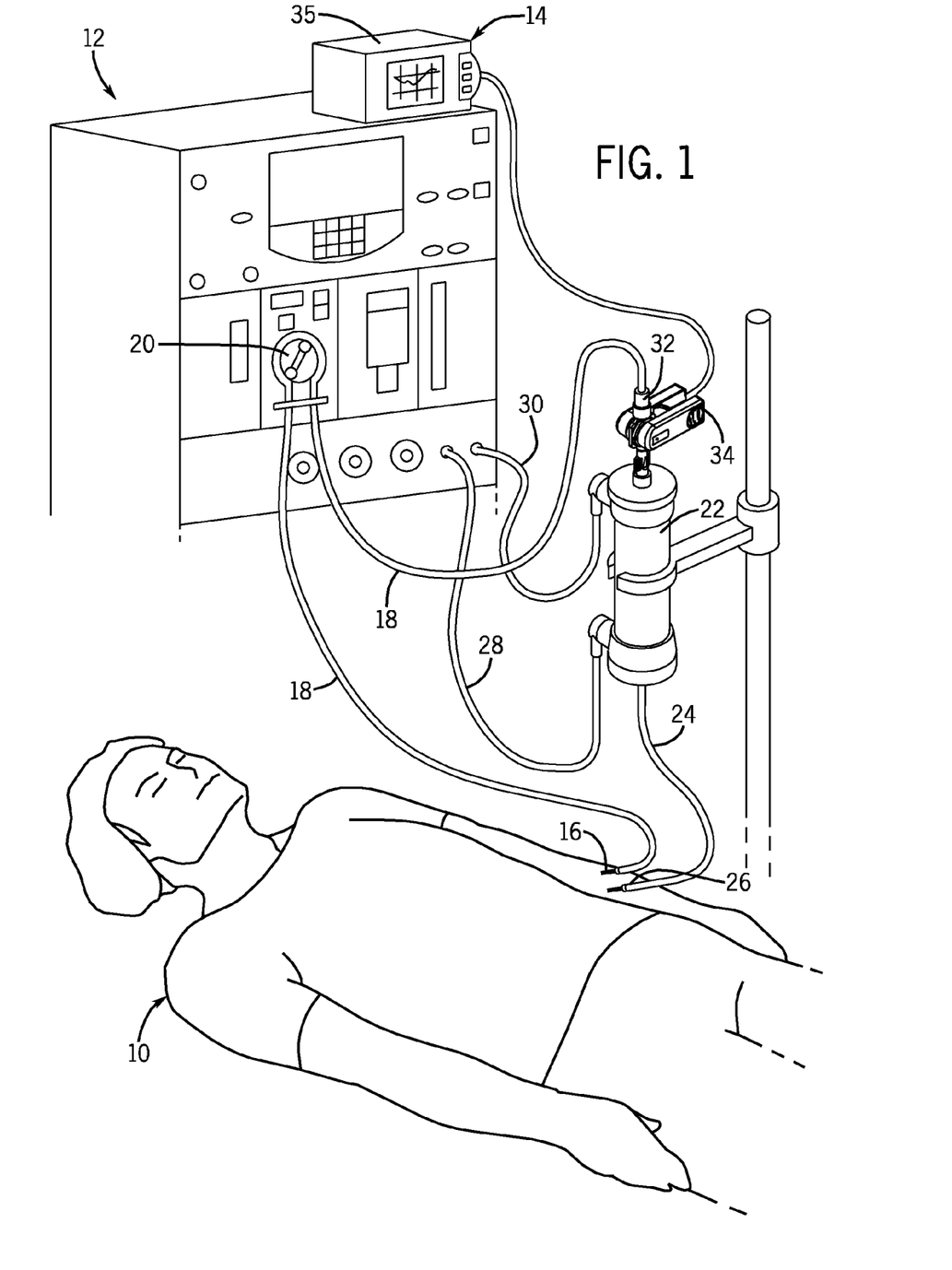
FIG. 1 is a perspective view of a patient undergoing hemodialysis treatment with a non-invasive, optical blood monitor monitoring the blood in real-time as it passes through extracorporeal tubing in the hemodialysis system.

FIG. 1 illustrates a patient 10 undergoing hemodialysis treatment using a conventional hemodialysis system 12, as well as a non-invasive, optical blood monitor 14. A typical hemodialysis clinic in the United States will have several hemodialysis systems 12 for treating patients.

An input needle (or catheter) 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer through extracorporeal tubing 24 and return needle (or catheter) 26. In some parts of the world, the extracorporeal blood flow may receive a heparin drip to prevent clotting although that is not shown in FIG. 1. The excess fluids and toxins are removed by clean dialysate liquid which is supplied to the dialyzer 22 via tube 28 and removed for disposal via tube 30. A typical hemodialysis treatment session takes about 3 to 5 hours in the United States.

The optical blood monitor 14 includes a blood chamber 32, an optical blood sensor assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photo emitters that emit light at substantially 810 nm, which is isobestic for red blood cells, substantially 1300 nm, which is isobestic for water, and at substantially 660 nm, which is sensitive for the oxygenation of hemoglobin. The blood chamber 32 includes lenses so that the sensor emitters and detectors can view the blood flowing through the blood chamber 32, and determine the patient's real-time hematocrit value and oxygen saturation value using ratiometric techniques generally known in the prior art.

Figure 2:
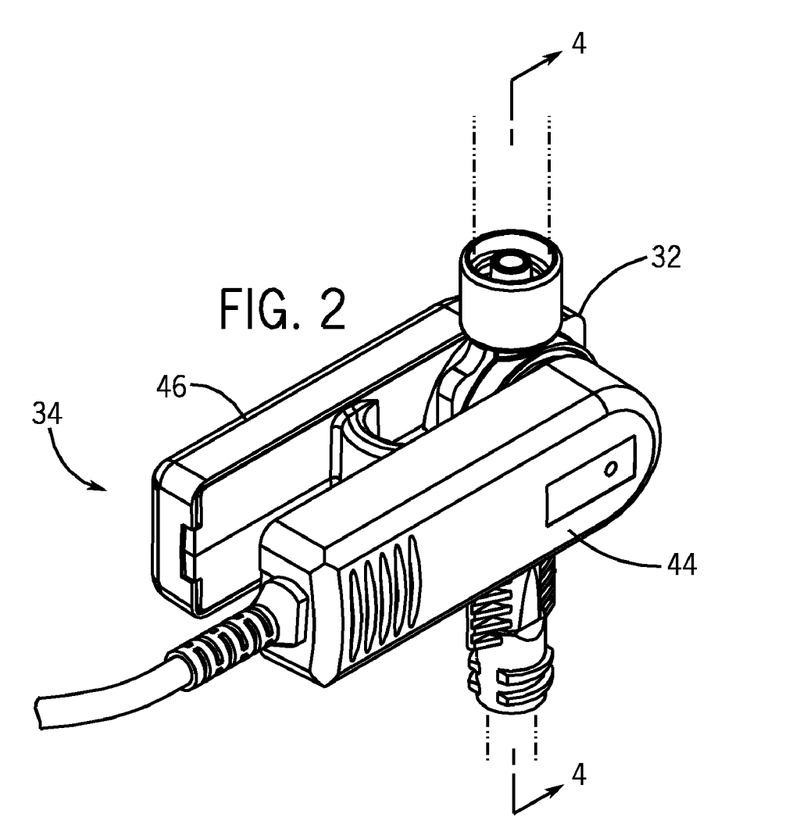
FIG. 2 is a perspective view showing a sensor assembly for the optical blood monitor positioned to sense blood flowing through a blood chamber connected in the extracorporeal tubing of the hemodialysis system.
Figure 3:
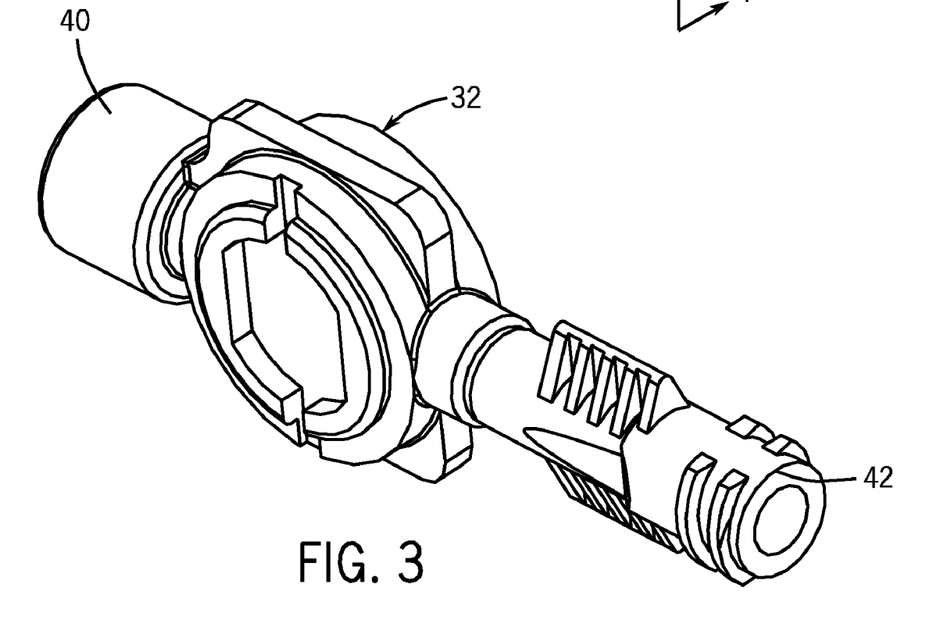
FIG. 3 is a detailed view of the blood chamber shown in FIG. 2.
Figure 4:
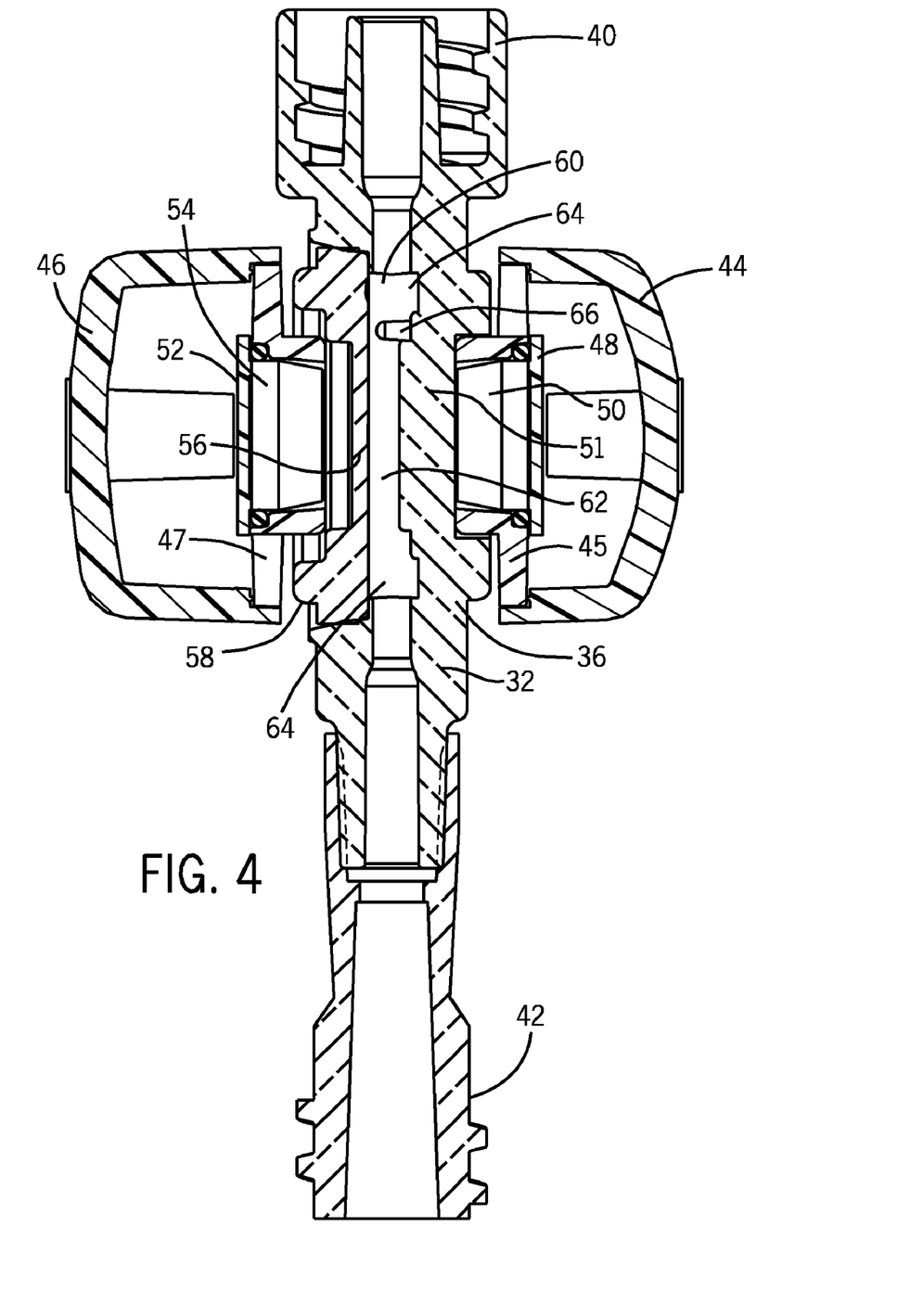
FIG. 4 is a cross-sectional view taken along line 4-4 in FIG. 2.

Referring to now FIGS. 2-4, the body of the blood chamber 32 is preferably made of molded polycarbonate. It includes two viewing windows 51, 56 (see FIG. 4). The inlet 40 and outlet 42 are designed to be compatible with standard medical industry connecting devices, conventionally known as Luer locks. In the blood chamber 32 shown in the drawings, the inlet 40 is integrally molded with the blood chamber 32, whereas the outlet 42 consists of a suitable off-the-shelf connection adapter glued to the body of the blood chamber 32. The sensor assembly 34 includes an emitter subassembly 44 and a detector subassembly 46. As best shown in FIG. 4, an emitter circuit board 48 containing LEDs emitting light at substantially 660 nm, 810 nm and 1300 nm, is mounted within the housing for the sensor subassembly 44. The LED circuit board 48 emits light through a lens 50 that is mounted between the circuit board 48 and the viewing window 51 for the blood chamber 32. The controller 35 controls the operation of the each of the respective LED emitters and detectors so as to de-commutate the independent wavelength measurements. Another circuit board 52 contains light detectors, one made of silicon to detect light intensity at 810 nm and 660 nm, and the other made of InGaAs to detect light intensity at 1300 nm. The detector circuit board 52 is mounted within the housing for the detector subassembly 46. A lens 54 is mounted between the detector circuit board 52 and the viewing window 56 in the blood chamber 32 in order to facilitate transmission of light at the respective wavelengths to the detectors on the circuit board 52. Note that the viewing window is molded as a separate insert 58 that is sonically welded to the body 36 of the blood chamber 32. As in the prior art, the blood flows from the inlet 40 through the passageway 60 to a central viewing region 62. The light at the three selected wavelengths, namely 810 nm, 1300 nm and 660 nm, are transmitted through the blood flowing through this portion 62 of the blood flow path, as well as the viewing windows 51, 56 in the chamber 32. The viewing region 62 provides a substantially flat, thin (e.g. less than 0.1 inches) viewing region for the blood flowing through the blood chamber 36. A moat 64 surrounds the flat viewing region 62. The moat 64 is somewhat deeper than the flat viewing region 62, and serves to distribute the flow evenly and steadily through the viewing region. The moat 64 also offers a degree of optical isolation from light piping in the polycarbonate. One or more protrusions 66 are located immediately upstream of the viewing region 62 so that the flow across the viewing region 62 is at least somewhat turbulent. While the flow across the viewing region 62 is preferably somewhat turbulent, the configuration of the blood chamber 32 shown in FIG. 4 results in a steady state flow through the viewing region 62 in terms of pressure and flow rate.

The housings 44 and 46 for the sensor assembly 34 include an inner housing piece 45, 47 which connects to the outer shells 44, 46. The inner housing components 45, 47 provide an opening into which the lenses 50, 54 are mounted. The sensor assembly 34 is preferably a spring loaded clip that can be mounted to the blood chamber 32, as shown in FIG. 2. Both sides of the blood chamber 32 are molded such that the clip 34 will reside in a predetermined position when mounted to the blood chamber 32. As mentioned, blood chamber 32 is a single-use, reusable polycarbonate component. Between patients, the blood chamber 32 is replaced as is the extracorporeal tubing 18, 24, and blood filter 22.

Figure 5:
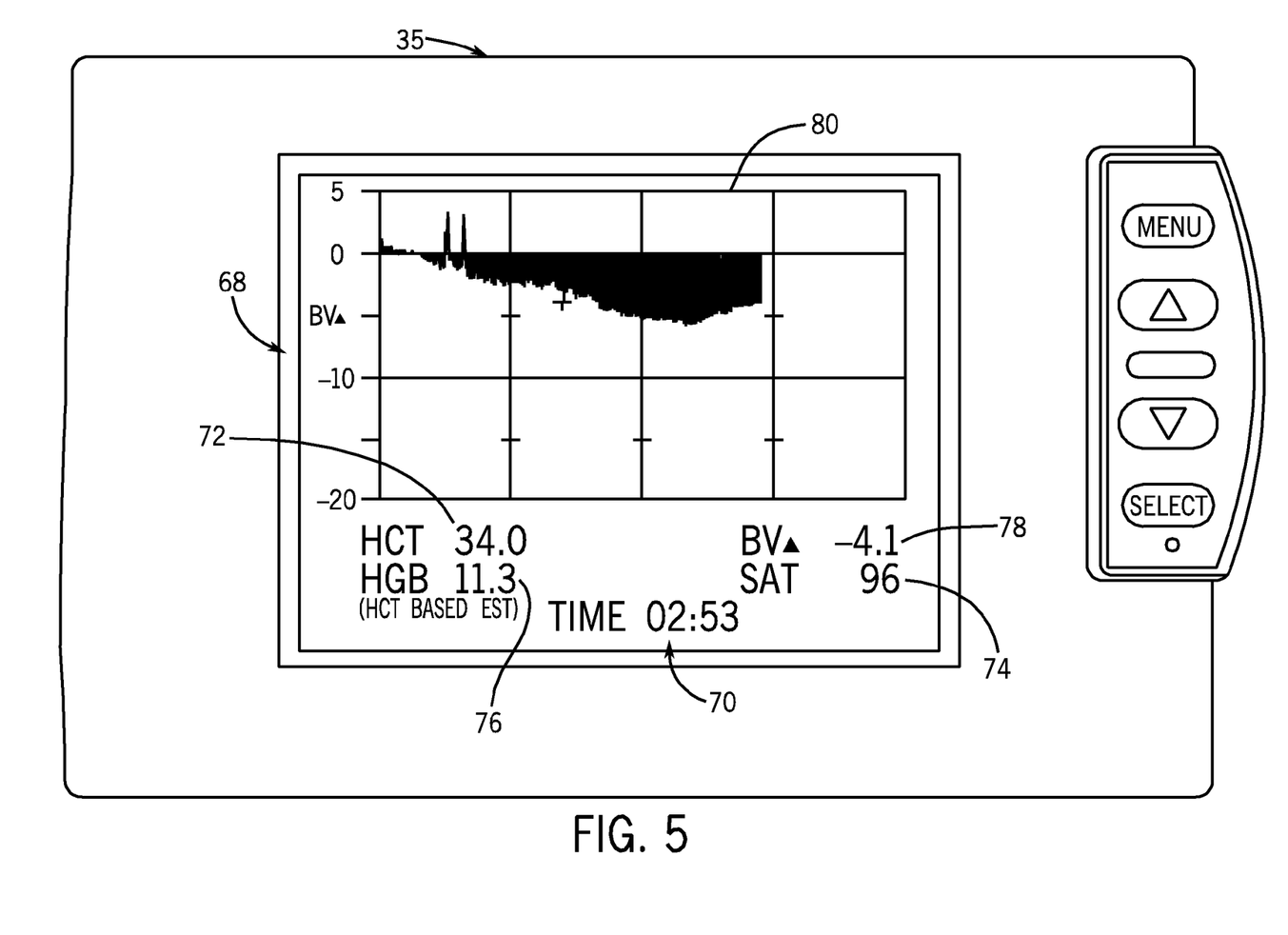
FIG. 5 is a front elevational view of the controller for the optical blood monitor illustrating data including real-time hematocrit (HCT), change in blood volume (BVΔ), hemoglobin (HBG), and oxygen saturation (SAT) levels, as well as the amount of time into the hemodialysis treatment session and a graphical representation of the change in blood volume during the course of the hemodialysis treatment session.

FIG. 5 is a front elevational view of the preferred controller 35 for the optical blood monitor 14. The controller 35 includes a display 68 which provides real-time blood monitoring data for the patient undergoing hemodialysis. The display in FIG. 5 illustrates the amount of time 70 that the patient 10 has been monitored while undergoing hemodialysis for the current treatment session. The time 70 displayed on the screen 68 in FIG. 5 is 2 hours and 53 minutes. The display 68 also illustrates real-time values for the optically monitored hematocrit (HCT) 72 and oxygen saturation (SAT) level 74, as well as the calculated values for hemoglobin (HGB) 76 and change in blood volume (BVΔ) during the treatment session 78. The graph 80 on the display 68 illustrates the change in the patient's blood volume over the course of the 2 hour and 53 minute treatment session. This data is displayed, as shown in FIG. 1, in a location that is located within the vicinity of the patient 10.

Periodically, the calibration and accuracy of the optical blood monitor 14 should be checked. In the art, this is normally done by placing the sensor clip 34 onto a verification filter (made of layered plastic having known optical qualities) that is mounted to the side of the monitor 14. Calibration software within the controller 35 will verify the calibration of the unit, or allow the user to field calibrate the unit within factory preset limits to bring it back to factory calibration settings. In some instances, when the preset limits are exceeded, it is necessary to return the unit to the factory for calibration.

Figure 6:
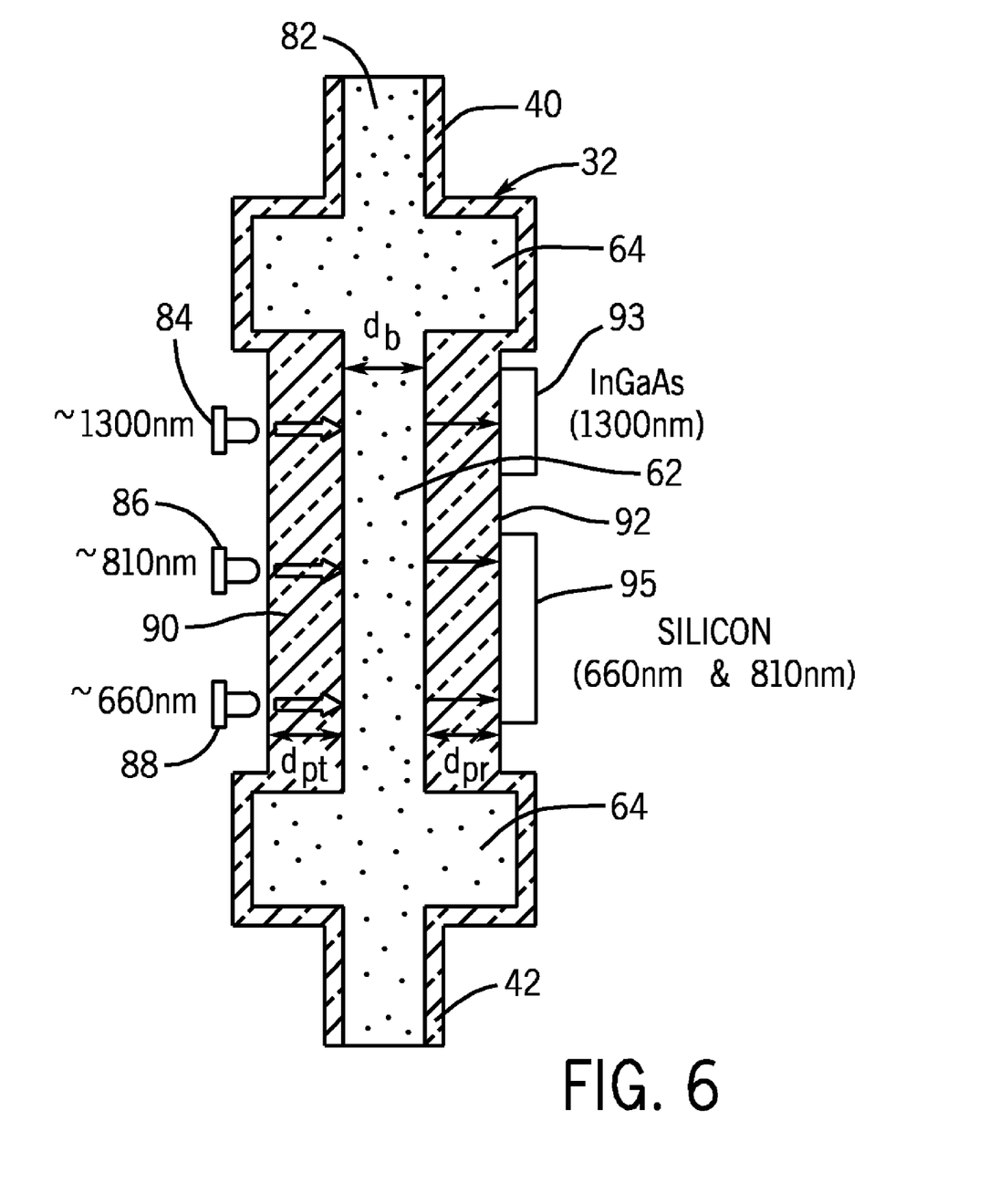
FIG. 6 is a schematic drawing illustrating the detection of light at various wavelengths through the blood chamber in order to monitor the hematocrit and oxygen saturation of the blood passing through the blood chamber.

FIG. 6 is a schematic illustration of the blood chamber 32 with a patient's blood 82 flowing through the chamber 32. As described above, the blood 82 enters the blood chamber through an inlet 40 and then flows into a moat 64 surrounding the viewing area 62. The distance across the viewing area is given by the arrow labeled $d_b$, which signifies the thickness of the blood flowing through the viewing area 62. After the blood leaves the viewing area 62, it flows into the moat 64 located on the other side of the viewing area 62 and out of the chamber through the outlet 42. FIG. 6 shows three LED emitters 84, 86 and 88. Emitter 84 emits light at substantially 1300 nm, emitter 86 emits light at substantially 810 nm, and emitter 88 emits light at substantially 660 nm. As mentioned, each of the emitters 84, 86, 88 emits light at a stable intensity. In one suitable approach, each of the emitters 84, 86, 88 are pulsed on for a time period such that it is on at a time when the other two emitters are not on (i.e., timed-based de-commutation), although other methods of de-commutation are possible. As shown in FIG. 6, the light from each emitter 84, 86, 88 is first transmitted through the polycarbonate transmission window 90 in the blood chamber 32. The light is then transmitted through the blood flowing through the viewing region 62 and is then transmitted through the polycarbonate receiving window 92 on the other side of the blood chamber 32. An indium gallium arsenide detector 93 detects the intensity of the 1300 nm light wave that is transmitted through the walls of the blood chamber and the blood flowing through the blood chamber 32. A silicon detector 95 detects the intensity of light at 810 nm and at 660 nm transmitted through the walls of the blood chamber and the blood flowing through the viewing region 92.

The intensity of the received light at each of the various wavelengths is reduced by attenuation and scattering from the fixed intensity of the light emitted from each of the emitters 84, 86, 88. Beers Law, for each wavelength of light, describes attenuation and scattering as follows:

$$i_n = I_{on} * e^{-\varepsilon_{pn} X_p d_{pt}} * e^{-\varepsilon_{bn} X_b d_{pt}} * e^{-\varepsilon_{pn} X_p d_{pr}} \quad \text{Eq. (3)}$$

where $i_n$=received light intensity at wavelength n after attenuation and scattering; $I_{on}$=transmitted light intensity at wavelength n incident to the measured medium; e=the natural exponential term; ε=the extinction coefficient for the measured medium (p—polycarbonate, b—blood) at wavelength n; X=the molar concentration of the measured medium (p—polycarbonate, b—blood); and d=the distance through the measured medium (pt—transmitting polycarbonate, b—blood, pr—receiving polycarbonate).

Since the properties of the polycarbonate blood chamber do not change during the measurements, the first and third exponential terms in the above Eq. (3) are constants for each wavelength. Mathematically, then these constant terms are multiplicative with the initial constant term $I_{on}$ which represents the fixed intensity of the light transmitted from the respective emitter 84, 86, 88. For simplification purposes, Eq. (3) can be rewritten in the following form using bulk extinction coefficients and a modified initial constant $I'_{on}$ as follows:

$$i_n = I'_{on} * e^{-\alpha_{bn} d_b} \quad \text{Eq. (4)}$$

where $i_n$=received light intensity at wavelength "n" after attenuation and scattering as though the detector were at the receive blood boundary; α=the bulk extinction coefficient (p—polycarbonate, b—blood) at wavelength n; $\alpha_{bn}=\varepsilon_{bn} X_b$; and $I'_{on}$=the equivalent transmitted light intensity at wavelength n as if applied to the transmit blood boundary accounting for losses through the blood chamber.

Note that the term $I'_{on}$ is the light intensity incident on the blood with the blood chamber losses included at wavelength n.

Using the approach defined in Eq. (4) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values α for the red blood cells and the water constituents in the blood chamber, respectively. The following mathematical function then defines the measured HCT value:

$$HCT = f\left[\frac{\ln\left(\frac{i_{800}}{I_{0800}}\right)}{\ln\left(\frac{i_{1300}}{I_{01300}}\right)}\right] \quad \text{Eq. (5)}$$

where $i_{800}$ is the light intensity of the photo receiver at 810 nm, $i_{1300}$ is the light intensity of the photo detector at 1300 nm and $I_{0800}$ and $I_{01300}$ are constants representing the light intensity incident on the blood accounting for losses through the blood chamber. The above equation holds true assuming that the flow of blood through the blood chamber 32 is in steady state, i.e. steady pressure and steady flow rate. This assumption is accurate in part because, as mentioned above, the moat 64 helps to maintain the blood flow in steady state.

The preferred function f is a second order polynomial having the following form:

$$HCT = f = A\left[\frac{\ln\left(\frac{i_{800}}{I_{0800}}\right)}{\ln\left(\frac{i_{1300}}{I_{01300}}\right)}\right]^2 + B\left[\frac{\ln\left(\frac{i_{800}}{I_{0800}}\right)}{\ln\left(\frac{i_{1300}}{I_{01300}}\right)}\right] + C. \quad \text{Eq. (6)}$$

A second order polynomial is adequate as long as the light incident at the first and second wavelengths is substantially isobestic. If the transmitted wavelengths for the first and second detectors 84, 86 are not substantially isobestic, then the hematocrit level will vary somewhat with oxygen level and vice versa. In that case, it is known to use a compensation matrix where coefficients A, B, C are the result of a second or higher polynomial based on the oxygen ratio shown in Eq. (7) in order to assure that the function f accurately calculates HCT in all circumstances.

The oxygen saturation level, or the oxygenated hemoglobin level, is determined using a ratiometric equation for the emitter 88 emitting light at 660 nm and the emitter 86 emitting light at 810 nm. The form of the preferred ratiometric model for determining oxygen saturation level is as follows:

$$SAT = g\left[\frac{\ln\left(\frac{i_{660}}{I_{0660}}\right)}{\ln\left(\frac{i_{800}}{I_{0800}}\right)}\right] \quad \text{Eq. (7)}$$

where $i_{660}$ is the light intensity of the photo receiver at 660 nm, $i_{800}$ is the light intensity of the photo detector at 800 nm and $I_{0660}$ and $I_{0800}$ are constants representing the intensity incident on the blood accounting for losses through the blood chamber. The function g is a mathematical function determined based on experimental data to yield the oxygen saturation level, again preferably a second order polynomial. It may be useful to use a pair of second order polynomials depending on the hematocrit value.

Referring again to the optical measurement of the HCT level, so long as the blood cells are uniform and without complications, Eq. (5) and (6) produces very good and repeatable results in the measurement of HCT. However, unhealthy or modified cells may manifest a different value of HCT. As mentioned above, in order to affect the HCT either the number of blood cells or the mean cell volume must change. When red blood cells are in the body or leave the body briefly for extracorporeal measurement, the body maintains the cells in the best conditions possible for the patient's current health state. On the other hand, when cells are removed from the body as a blood sample for the purpose of in vitro measurement in a laboratory or to be stored for transfusion at a later time, cell conditions can be compromised. Normally, blood removed from the body will clot in a very short time, a function of multiple cells bonding and then rupturing. To preserve blood for a period for time, anticoagulants are used. There are a number of types of anticoagulants used in the art, each affects the blood differently and may be used for different purposes.

In the process of calibrating the optical blood monitor 14, it is common, due to availability, to use blood bank blood preserved in citrate phosphate dextrose (CPD). The use of blood bank blood removes the need to have a ready supply of human donors to give blood each time the optical blood monitors need to be calibrated at the factory. As mentioned, long-term storage of blood requires the use of an anticoagulant to keep the cells from bonding together (clotting) and a method of feeding the cells to keep them alive. The most common long-term anticoagulant used on blood bank blood is citrate phosphate dextrose (CPD). Blood kept in CPD should remain good for approximately 28 days after donation.

In order to calibrate the optical blood monitor 14, the unit is first tested with synthetic filters having known optical transmission. A predetermined target value selected for $I_{0800}$, inasmuch as this value is used for both the ratiometric model for the HCT and the ratiometric model for the SAT. (This value is estimated by measuring normal saline or distilled water filling a blood chamber 32. Since $\alpha_{0800}$ for normal saline or water is substantially zero, from Eq. (4) $I_{0800}$ is approximately equal to $i_{800}$. Then using the synthetic filters, the ratiometric model for HCT is initially calibrated by adjusting the value of $I_{01300}$ in order that the HCT value output from the system corresponds to the known percent transmissivity for each of a high and a low synthetic filters. Then, a group of the optical blood monitors (e.g., a group of six monitors) is calibrated using blood from a blood bank which is preserved in CPD with preserving salts not added. A sample of the same blood supply is also tested in a Coulter counter.

More specifically, in order to calibrate the optical blood monitors, hemo-concentrated blood preserved in CPD (without preserving salts) is obtained from a blood bank. The hemo-concentrated blood is diluted with normal saline to generate different blood samples having various hematocrit values, typically between 12 to 58. The optical blood monitors in the group are then baselined against a Coulter counter using four data points. In other words, the optical blood monitors in the group are calibrated in order that there is full 1:1 agreement at four points, namely at four different hematocrit values ranging between 12 to 58. The next group of optical blood monitors may be calibrated with different four points; however, the calibration will again require 1:1 correspondence at four points with the Coulter counter on the saline-diluted blood samples. The Coulter counter itself should be calibrated from time to time, as is known in the art, and it may also be desirable to check the Coulter counter against another Coulter counter periodically.

As mentioned previously, the chemical effect of CPD on red blood cells differs from the chemical effect of shorter term anticoagulants such as potassium ethylene diamine tetra acetic ($K_3EDTA$), which is the anticoagulant found in a standard purple-top vacuum container used for common blood draws in a clinic. In the prior art, when blood is read in a laboratory from a purple-top test tube, the results tend to be slightly higher than the results read on an optical blood monitor that was calibrated using samples of saline-diluted hemo-concentrated blood from a blood bank preserved in CPD. For example, laboratory work on whole blood which is not stored in a preservative might result in an HCT of 32, whereas blood from the same patient stored in a purple-top test tube ($K_3EDTA$) might result in an HCT value of 31, and if preserved in CPD might result in an HCT value of 30, all because of the different red blood cell morphology caused by the different preservatives.

Figure 7:
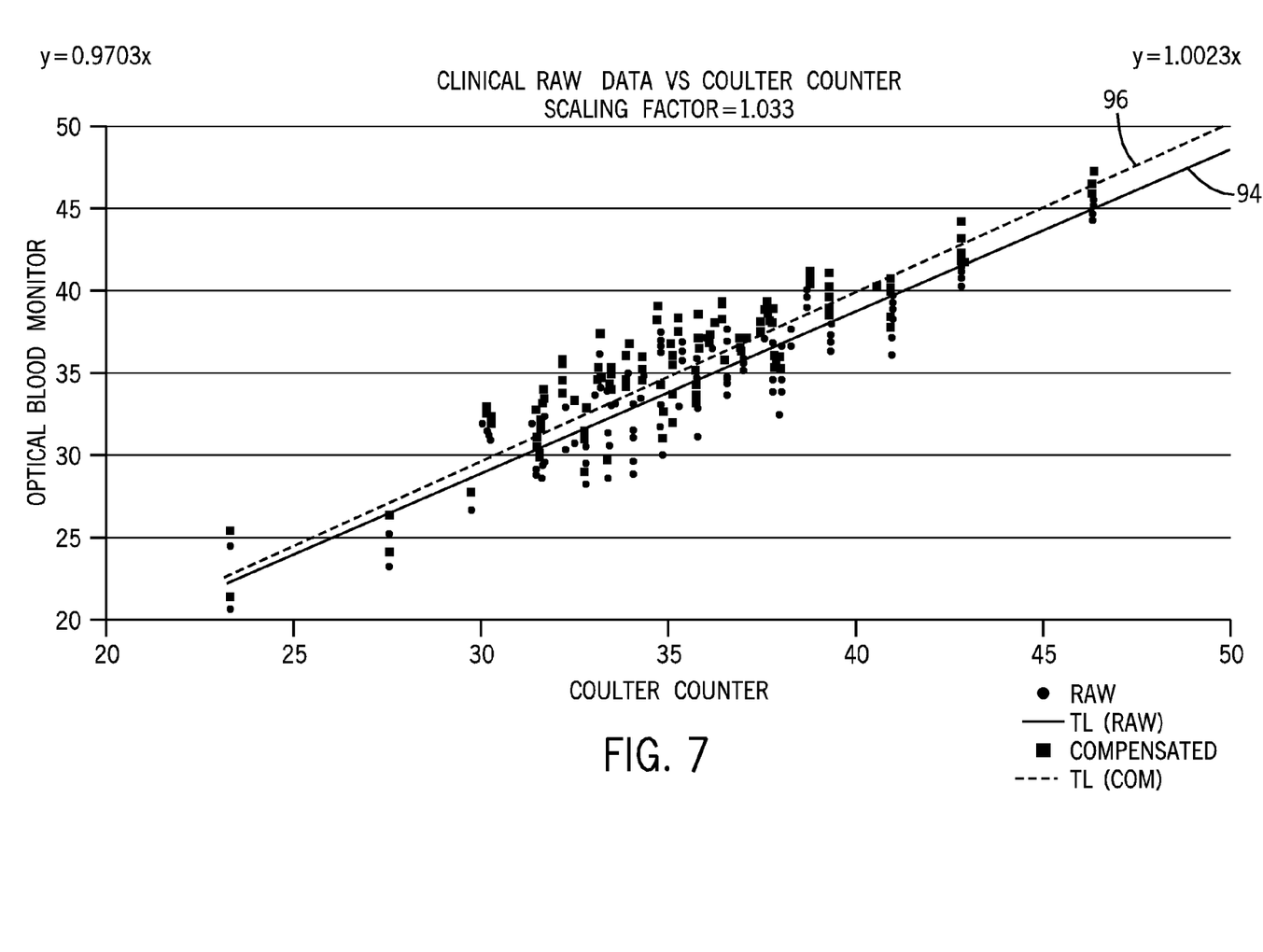
FIG. 7 is a plot of data showing a linear regression analysis for raw data and data scaled to compensate for the difference in preservatives between blood used to calibrate optical blood monitoring equipment and blood taken from a patient in a clinic.

FIG. 7 shows a plot of data taken to determine the relative effects of CPD and $K_3EDTA$. The test data compares hematocrit values taken from a number of patients (i.e., 50) using several optical blood monitors. During the test, data was taken from the patients using a Coulter counter, on the one hand, and an optical blood monitor on the other. Along the x-axis are plotted values for the hematocrit as measured from a blood sample taken from a patient and stored in a purple-top test tube (i.e. $K_3EDTA$) preservative. Along the y-axis are plotted optically measured hematocrit values taken at the same time as the blood draw from the patient. The optical blood monitor was calibrated in each case using blood bank blood preserved in CPD, as described above. Of course, the blood actually measured by the optical blood monitor is flowing through a hemodialysis loop, and does not contain any preservative or anticoagulant except for heparin that is added into the hemodialysis drip as a standard procedure. The data illustrated by the round dots in FIG. 7 is the raw clinical data collected by the optical monitor as compared to the raw clinical data collected by the Coulter counter. Line 94 represents the best fit of the raw data collected. The line 94 is represented by the equation y=0.9703*x, which is a linear expression without an offset. In other words, the optical blood monitor typically measured about 3% low compared to the Coulter counter, even though the optical blood monitor was calibrated 1:1 to the same Coulter counter during the original calibration in the factory using saline-diluted, hemo-concentrated blood from a bank blood preserved in CPD.

FIG. 7 also shows square data points, which are scaled to increase the value detected by the optical blood monitor by a factor of 1.033. Line 96 represents a regression of the scaled data. Line 96 is represented by the equation y=1.0023*x, thereby indicating that the scaled data from the optical blood monitor is not biased above or below the Coulter counter collected data. Therefore, in order for the output HCT value from the optical blood monitor to match the hematocrit measured from blood stored in the purple-top test tube (i.e. $K_3EDTA$), the hematocrit value should be scaled by a factor 1.03 before it is displayed to the user of the optical blood monitoring system 14. In the preferred commercial embodiment of the invention, the displayed HCT value is adjusted to display $HCT_s$ where $HCT_s$ the scaled hematocrit value. The scaled hematocrit value is also used to determine the estimated Hgb value, i.e. $Hgb = HCT_s/2.941$.

The inventors have also run similar tests comparing the output of the calibrated optical blood monitors to the results of in vitro testing of whole blood without any anticoagulants whatsoever. This test had similar results, with the scaling factor being 1.06 to match in vitro hematocrit values measured by the Coulter counter.

In additional testing, it was found that heparin has no effect, and therefore no scaling factor is necessary to account for the effects of heparin.

It should be appreciated that the present invention contemplates the use of scaling factors in order to compensate for various other types of preservatives or anticoagulants that may be used during the course of calibrating optical blood monitoring equipment, or when sampling blood from a patient for in vitro laboratory tests.

It also may be desirable, as mentioned above, to correct the estimated hemoglobin value for changes in altitude. It is well known that residence at a high altitude exposes a person to relative hypoxia compared to what the same person would experience at sea level. This results in a slightly higher hemoglobin level in the blood for the person residing at high altitudes. The hemoglobin correction in gm/dl can be given by the following expression:

$$\text{Correction (gm/dl)} = 0.00000016 * E^2 + 0.00016113 * E + 0.04359886 \qquad \text{Eq. (8)}$$

where E is the elevation in meters. The above hemoglobin correction method is disclosed in Dirren H, Logman MHGM, et al., Altitude Correction For Hemoglobin, European Journal of Clinical Nutrition, 1994, 48:625-632. The above hemoglobin altitude correction algorithm can be used to adjust the value at an altitude to the comparable value at sea level by adding the correction factor, or vice versa by subtracting the correction factor. The correction factor would thus preferably be determined upon installation of the optical blood monitor, by programming the optical blood monitor with the altitude at which it will be operated after installation. Preferably, the hemoglobin value displayed on the optical monitor is in the first instance based on a scaled hematocrit value, and then adjusted by the appropriate correction factor for altitude, prior to being displayed.

When a typical patient 10 arrives at a hemodialysis clinic, the patient is first checked in and then weighed on a scale at the clinic. The patient then is seated in an assigned hemodialysis chair where a clinician inserts an arterial and venous needle into the patient's access. Next, the dialysis lines 18, 24 are prefilled with normal saline and connected to the patient. The peristaltic pump 20 is started slowly and the normal saline is flushed through the lines 18, 24 as well as the dialyzer 22 into the patient 10, as arterial blood is pulled into the dialysis circuit. The normal saline tends to lubricate or prime the system for blood passage. Also, since saline is less dense than blood, any leaks in the system will be immediately apparent.

The clinician then waits approximately 5 minutes for the hematocrit (HCT) of the patient's body to stabilize after the saline has been infused. The saline must mix out in the patient's body in order to obtain a stable reading for the hematocrit (HCT) at the onset of the hemodialysis process. During this wait time, the clinician presses the menu button on the monitor 14 and enters the patient ID number. While it would be technically possible to enter the patient's name in lieu of a patient ID number, it is preferable to enter a patient ID number in order to accommodate patient privacy laws. Once approximately 5 minutes have passed after the saline prime is flushed into the body, the patient's data run begins. The optical blood monitor controller 35 is turned on to measure and store in memory initial values for hematocrit (HCT), hemoglobin (Hgb), and oxygen saturation (SAT) levels. As mentioned, the hemoglobin level is estimated from the measured and scaled hematocrit ($HCT_s = 2.941*Hgb$ at sea level), and then preferably adjusted to account for altitude above sea level.

After the initial levels for hematocrit, hemoglobin and oxygen saturation are measured and stored in the controller 35, the ultra filtration rate (UFR) on the dialysis machine is advanced, causing an osmosis vacuum to form across the dialyzer 22. From that point on, fluid is removed from the blood, but red blood cells are preserved within the body. Staff monitors the patient's HCT, Hgb, SAT and BVΔ during the hemodialysis process to ensure that the patient is performing well during the treatment session. At the end of treatment, the hemodialysis system 12 is stopped after the blood is drained from the lines into the venous needle 26 of the patient 10. The patient is allowed to sit for a while, and the clinical staff assesses the patient's conditions while they remove the needles, bandage the patient, and check for bleeding. The patient is then weighed again at the end of the treatment, and perhaps a physician prescribes the administration of an ESA dose. Normally, the physician would consider the patient's Hgb level taken at the start of the treatment session when prescribing ESA dosage or other therapeutic care. The patient 10 then receives their prescribed dose and is released to go.

The described use and embodiment of the invention is to be considered in all respects as only illustrative and not restrictive.

We claim:

1. In a hemodialysis system, a method for monitoring at least one blood constituent, the method comprising the steps of:
   providing a blood chamber in extracorporeal tubing through which a patient's blood flows for hemodialysis;
   providing a ratiometric model within a controller for an optical monitoring device that determines a hematocrit value as a function of at least a detected value of light intensity having a first wavelength and a detected value of light intensity having a second wavelength, wherein the ratiometric model is calibrated at least in part by testing the ratiometric model by using the optical monitoring device with whole blood from a supply of blood preserved in a first anticoagulant, measuring the hematocrit value of whole blood from the same supply of blood preserved in the first anticoagulant using an in vitro method, and calibrating the ratiometric model to the measured hematocrit value taken using the in vitro method;
   emitting light at a first wavelength through the extracorporeal blood chamber and the patient's blood flowing through the blood chamber;
   emitting light at the second wavelength through the extracorporeal blood chamber and the patient's blood flowing through the blood chamber;
   detecting the intensity of the light at the first wavelength after it has passed through the extracorporeal blood chamber and the patient's blood flowing therethrough;
   detecting the intensity of the light at the second wavelength after it passes through the extracorporeal blood chamber and the blood flowing therethrough;
   calculating a hematocrit value using the ratiometric model from at least the detected light intensity at the first wavelength and the detected light intensity at the second wavelength; and
   scaling the hematocrit value calculated by the ratiometric model by a scaling factor to result in a scaled hematocrit value that accounts for a second anticoagulant in the patient's blood.

2. The method as recited in claim 1 wherein the flow of blood through the blood chamber is assumed to be at a steady state during the monitoring process and wherein the ratiometric model is of the following form:

$$HCT = f\left[\frac{\ln\left(\frac{i_{\lambda 1}}{I_{0\lambda 1}}\right)}{\ln\left(\frac{i_{\lambda 2}}{I_{0\lambda 2}}\right)}\right]$$

where HCT is the hematocrit value determined by the ratiometric model;
$i\lambda 1$ is the detected light intensity at first wavelength;
$i\lambda 2$ is the detected light intensity at the second wavelength;
$I0\lambda 1$ is a constant representing the light intensity of the first wavelength incident on the blood chamber taking into account the losses due to the blood chamber;
$I0\lambda 2$ is a constant representing the light intensity of the second wavelength incident on the blood chamber taking into account the losses due to the blood chamber; and
f is a function that fits log ratio mathematics to yield HCT.

3. A method as recited in claim 2 wherein during initial calibration of the ratiometric model the value $I_{0\lambda 1}$ is set to a predetermined value and the ratiometric model is calibrated by adjusting $I_{0\lambda 2}$ until the hematocrit value output from the model matches the hematocrit value determined by the in vitro method.

4. A method as recited in claim 2 wherein the light intensity of the first wavelength is substantially isobestic for red blood cells and the light intensity of the second wavelength is substantially isobestic for water, and the function f is a second order polynomial.

5. A method as recited in claim 4 wherein the function f is defined by the following equation:

$$HCT = f = A\left[\frac{\ln\left(\frac{i_{\lambda 1}}{I_{0\lambda 1}}\right)}{\ln\left(\frac{i_{\lambda 2}}{I_{0\lambda 2}}\right)}\right]^2 + B\left[\frac{\ln\left(\frac{i_{\lambda 1}}{I_{0\lambda 1}}\right)}{\ln\left(\frac{i_{\lambda 2}}{I_{0\lambda 2}}\right)}\right] + C.$$

6. A method as recited in claim 1 wherein the first wavelength is approximately 800 nm, the second wavelength is approximately 1300 nm, and the method further comprises emitting light at a third wavelength through the extracorporeal blood chamber and blood flowing therethrough, and detecting the intensity of the light at the third wavelength, and determining oxygen saturation levels based on the detected light intensity at the first wavelength and the detected light intensity at the third wavelength.

7. A method as recited in claim 1 wherein the first anticoagulant is citrate phosphate dextrose, the scaling factor is substantially about 1.033 in order that the scaled hematocrit value output from the monitor matches the measured hematocrit value of blood taken from the patient and preserved with potassium ethylene diamine tetra acetic when measured using the in vitro method.

8. A method as recited in claim 1 wherein the first anticoagulant is citrate phosphate dextrose, the scaling factor is substantially about 1.06 in order that the scaled hematocrit value output from the monitor matches the hematocrit value of blood taken from the patient without the addition of anticoagulant or preservative when measured using the in vitro method.

9. A method as recited in claim 1 wherein the method further comprises the step of dividing the scaled hematocrit value by a constant substantially equal to 2.94 in order to estimate the patient's hemoglobin value.

10. A method as recited in claim 1 wherein the value of the scaling factor is determined based on statistical analysis of test data on a variety of blood samples.

11. A method as recited in claim 1 wherein the blood used to calibrate the ratiometric model is preserved in citrate phosphate dextrose, without additional preserving salts.

12. For use with a hemodialysis system that draws blood from a patient, passes the drawn blood through extracorporeal tubing and through a dialyzer, and returns the dialyzed blood through extracorporeal tubing to the patient, a optical blood monitor associated with the hemodialysis system, the monitor comprising:
   a sensor assembly that monitors the patient's blood flowing through the hemodialysis system, the sensor comprising:
   a blood chamber having an inlet and an outlet which are connected inline with extracorporeal tubing for the hemodialysis system, and a fluid passageway through which the drawn blood from the patient flows,
   a first photo emitter for emitting light at a first wavelength through the blood chamber and the drawn blood flowing through the blood chamber,
   a second photo emitter for emitting light at a second wavelength through the blood chamber and the drawn blood flowing through the blood chamber, and
   at least one photo detector for detecting the intensity of the light at each wavelength after it passes through the blood chamber and the drawn blood;
   a controller that comprises a ratiometric model that calculates an hematocrit value as a function of at least a detected value of light intensity at the first wavelength and a detected value of light intensity at the second wavelength, wherein the ratiometric model is calculated at least in part by testing the ratiometric model with whole blood from a supply of blood preserved in a first anticoagulant and measuring the hematocrit value of whole blood from the same supply of blood preserved in the first anticoagulant using an in vitro method, and calibrating the ratiometric model to the hematocrit value measured using the in vitro method, and further wherein the controller comprises means for scaling the hematocrit value calculated by the ratiometric model by a scaling factor to account for a second anticoagulant in the patient's blood.

13. An optical blood monitor as recited in claim 12 wherein the ratiometric model is of the following form:

$$HCT = f\left[\frac{\ln\left(\frac{i_{\lambda 1}}{I_{0\lambda 1}}\right)}{\ln\left(\frac{i_{\lambda 2}}{I_{0\lambda 1}}\right)}\right]$$

$i_{\lambda 1}$ is the detected light intensity at the first wavelength;

$i_{\lambda 2}$ is the detected light intensity at the second wavelength;

$I_{0\lambda 1}$ is a constant representing the light intensity of the first wavelength incident on the blood chamber taking into account the losses due to the blood chamber;

$I_{0\lambda 2}$ is a constant representing the light intensity of the second wavelength incident on the blood chamber taking into account the losses due to the blood chamber; and f is a function that fits log ratio mathematics to yield HCT.

14. An optical blood monitor as recited in claim 13 wherein the first wavelength is substantially isobestic with red blood cells and the second wavelength is substantially isobestic with water, and the function f is a second order polynomial.

15. An optical blood monitor as recited in claim 14 wherein the function f is defined by the following equation:

$$HCT = f = A\left[\frac{\ln\left(\frac{i_{\lambda 1}}{I_{0\lambda 1}}\right)}{\ln\left(\frac{i_{\lambda 2}}{I_{0\lambda 2}}\right)}\right]^2 + B\left[\frac{\ln\left(\frac{i_{\lambda 1}}{I_{0\lambda 1}}\right)}{\ln\left(\frac{i_{\lambda 2}}{I_{0\lambda 2}}\right)}\right] + C.$$

16. An optical blood monitor as recited in claim 14 wherein the sensor assembly further comprises a third photo emitter for emitting light at a third wavelength through the blood chamber and the drawn blood flowing through the blood chamber, and further wherein the sensor assembly includes a photo detector that can detect the intensity of the third wavelength after it passes through the blood chamber and the drawn blood for measurement of oxygen saturation.

17. An optical blood monitor as recited in claim 16 wherein the first wavelength is approximately 800 nm, the second wavelength is approximately 1300 nm and the third wavelength is approximately 660 nm.

18. An optical blood monitor as recited in claim 14 wherein the first wavelength is approximately 810 nm and the second wavelength is approximately 1300 nm.

19. An optical blood monitor as recited in claim 14 wherein the predetermined proportionality factor is substantially about 1.033 in order that the adjusted hematocrit value output from the monitor matches measured hematocrit value of blood taken from the patient and stored in a test tube containing potassium ethylene diamine tetra acetic when measured using an in vitro method.

20. An optical blood monitor as recited in claim 14 wherein the predetermined proportionality factor is substantially about 1.06 in order that the adjusted hematocrit value output from the monitor matches measured hematocrit value of blood taken from the patient without being treated with anticoagulant or preservatives when measured using an in vitro method.

* * * * *